United States Patent
Van Mechelen

(10) Patent No.: US 10,041,785 B2
(45) Date of Patent: Aug. 7, 2018

(54) SENSOR SYSTEM AND METHOD FOR CHARACTERIZING A STACK OF WET PAINT LAYERS

(71) Applicant: ABB Schweiz AG, Baden (CH)

(72) Inventor: Jacobus Lodevicus Martinus Van Mechelen, Regensdorf (CH)

(73) Assignee: ABB Schweiz AG, Baden (DE)

( * ) Notice: Subject to any disclaimer, the term of this patent is extended or adjusted under 35 U.S.C. 154(b) by 36 days.

(21) Appl. No.: 15/555,429

(22) PCT Filed: Mar. 3, 2015

(86) PCT No.: PCT/EP2015/054352
§ 371 (c)(1),
(2) Date: Sep. 1, 2017

(87) PCT Pub. No.: WO2016/138935
PCT Pub. Date: Sep. 9, 2016

(65) Prior Publication Data
US 2018/0038681 A1    Feb. 8, 2018

(51) Int. Cl.
*G01B 11/06* (2006.01)
*G01N 33/32* (2006.01)
(Continued)

(52) U.S. Cl.
CPC ...... *G01B 11/0633* (2013.01); *G01B 11/0683* (2013.01); *G01N 21/3581* (2013.01);
(Continued)

(58) Field of Classification Search
CPC .................................................. G01B 11/0633
See application file for complete search history.

(56) References Cited

U.S. PATENT DOCUMENTS

| | | | |
|---|---|---|---|
| 6,092,419 A | 7/2000 | Dixon et al. | |
| 2012/0123707 A1* | 5/2012 | Bucher | G01B 11/0608 702/55 |
| 2012/0326037 A1* | 12/2012 | Ohtake | G01B 11/0633 250/338.1 |

FOREIGN PATENT DOCUMENTS

| EP | 2213977 A1 | 8/2010 |
|---|---|---|
| EP | 2899497 A1 | 7/2015 |
| JP | 2004028618 A | 1/2004 |

OTHER PUBLICATIONS

Ke Su, Yao-Chun Shen, J. Axel Zeitler, "Terahertz Sensor for Non-Contact Thickness and Quality Measurement of Automobile Paints of Varying Complexity", IEEE Transactions on Terahertz Science and Technology, vol. 4, Jul. 2014.*

(Continued)

*Primary Examiner* — Hugh H Maupin
(74) *Attorney, Agent, or Firm* — Whitmyer IP Group LLC

(57) ABSTRACT

A method of characterizing a wet paint layer stack of a painted body by individual parameters of the wet paint layers, based on fitting to a physical model, is provided. The method includes: emitting a THz radiation signal towards the painted body such that the THz radiation interacts with the wet paint layer stack; detecting a response signal being the detected THz radiation signal having interacted with the wet paint layer stack; determining model parameters of the physical model by optimizing the model parameters such that a predicted response signal of the physical model is fitted to the detected response signal, at least some of the model parameters being indicative of optical properties of the wet paint layers and of a wet paint layer thickness; and determining, from the determined model parameters, the individual paint layer parameters of at least one of the wet paint layers.

17 Claims, 5 Drawing Sheets

(51) Int. Cl.
  *G01N 21/3581* (2014.01)
  *G01N 21/59* (2006.01)
  *G01N 21/84* (2006.01)
(52) U.S. Cl.
  CPC .............. *G01N 21/59* (2013.01); *G01N 33/32* (2013.01); *G01N 2021/8438* (2013.01)

(56) References Cited

OTHER PUBLICATIONS

Tetsuo Iwata et al: "Prediction of the Thickness of a Thin Paint Film by Applying a Modified Partial-Least-Squares-1 Method to Data Obtained in Terahertz Reflectometry" Journal of Infrared, Millimeter and Terahertz Waves, Springer New York LLC, US. Published: Aug. 14, 2013, vol. 34, No. 10 14 Pages.
Yasui T. et al: "Terahertz Paintmeter for Noncontact Monitoring of Thickness and Drying Progress in Paint Film" Applied Optics, Optical Society of America, Washington, D.C.; vol. 44, No. 32 Published: Nov. 10, 2005 8 Pages.
International Search Report & Written Opinion Application No. PCT/EP2015/054352 Completed Dated: Oct. 5, 2015; dated Oct. 16, 2015 11 Pages.

* cited by examiner

SENSOR SYSTEM AND METHOD FOR CHARACTERIZING A STACK OF WET PAINT LAYERS

TECHNICAL FIELD

Aspects of the invention relate to a method for characterizing a wet paint layer stack of a painted body such as a painted automobile component, by means of THz radiation. More precisely, the method includes analyzing a detected THz radiation signal having interacted with the wet paint layer stack. Further aspects of the invention relate to a corresponding method of painting a body, to a corresponding sensor system, and to a corresponding painting facility for painting a body.

BACKGROUND

The application of polymeric coating, and in particular paint, can be useful for augmenting protection and aesthetics of a body, or for preparing the body for further processes such as application of further layer(s). In the following, mainly the case of the polymeric coating being a paint film is discussed, but the discussion also applies to bodies coated by other polymeric coatings.

Although the painting industry is more and more automatized by using paint robots, many paint films still show failures in the uniformity or visual appearance of the paint, or are painted on substrates which contain defects themselves. For these reasons, accurate quality control of paint films is an important part of the paint process. One important aspect of quality control is the measurement of the paint thickness, in order to ensure a uniform thickness within a predetermined tolerance range.

Car bodies are typically covered with a number of different layers which each have their own functionalities. Traditionally, each layer has to dry before a next layer can be sprayed on top. Since this is very time consuming, industrial paint lines utilize the more and more the so-called wet-on-wet technique. The idea of this technique is that a next layer is sprayed on a previous one while the latter is still relatively wet, which reduces the painting lead time between two layers drastically. Before curing, the automobile body then contains a multilayer of relatively wet layers on which early quality control is necessary.

Most state-of-the-art techniques for thickness determination determine just the total thickness of the entire paint film. Further, many of these techniques, such as acoustic and magnetic sensing, work only in contact mode. Furthermore, these techniques are paint unspecific, i.e. unable to account for specific properties of particular paint compositions, which results in large error bars, especially for thick layers and multilayers of different paints.

To overcome some of these limitations, recently methods based on THz radiation have been proposed. These THz based new methods allow non-contact measurements and thereby overcome an important drawback of the prior art. For example, JP 2004028618 A and EP 2213977 A1 describe respective methods for determining the thickness of a paint film using THz radiation. The thickness is obtained by subtraction of peak positions of a time-domain signal. The peak positions, together with a known group index of refraction of the paint, allow calculation of the thickness. However, the robustness of this method leaves room for improvement. Also, the method is only reliable for single layers of known paints with a known index of refraction, which is however typically not known. However, in industrial applications such as car body painting as cited above, typically a number of paint layers of various types are applied before the previously applied layer(s) have dried, which is not addressed properly by the known techniques.

Hence, known techniques for paint layer characterization leave room for improvement.

SUMMARY

In view of the above, a method of characterizing a wet paint layer stack of a painted body, a method of painting a body, a sensor system for characterizing a wet paint layer stack on a painted body, and a painting facility are provided.

According to a first aspect, a method of characterizing a wet paint layer stack of a painted body is provided, which comprises at least two wet paint layers, by individual parameters of the wet paint layers, based on fitting to a physical model, the method being carried out by a sensor system in a non-contact manner, the sensor system comprising an emitter system for emitting THz radiation, a detector system for detecting THz radiation, and a processing unit operationally coupled to the emitter system and the detector system. The method comprises: Emitting, by the emitter system, a THz radiation signal towards the painted body such that the THz radiation interacts with the wet paint layer stack, detecting, by the detector system, a response signal being the detected THz radiation signal having interacted with the wet paint layer stack; Determining model parameters of the physical model by optimizing the model parameters such that a predicted response signal of the physical model, which approximates the interaction of the THz radiation signal with the wet paint layer stack, is fitted to the detected response signal, wherein at least some of the model parameters are indicative of individual optical properties of the wet paint layers and of a wet paint layer thickness; and Determining, from the determined model parameters, the individual paint layer parameters of at least one of the wet paint layers.

According to a second aspect, a method of painting a body is provided. The method comprises: Applying at least two paint layers to the body, thereby producing a wet paint layer stack on the body; Characterizing the wet paint layer stack by the method according to any one of the preceding claims, thereby obtaining the paint layer parameters including a predicted dry paint layer thickness of one of the paint layers and/or of the wet paint layer stack; Further processing the painted body in dependence of the obtained paint layer parameters.

According to a third aspect, a sensor system for characterizing a wet paint layer of a painted body is provided. The sensor system comprises: an emitter system for emitting THz radiation towards the painted body; a detector system for detecting THz radiation coming from the painted body; a positioning system for positioning the emitter system and the detector system relative to the painted body; and a processing unit operationally coupled to the emitter system and the detector system. The sensor system is configured for characterizing the painted body by the method according to the first aspect.

According to a fourth aspect, a painting facility for painting a body is provided. The painting facility comprises: a painting device for applying paint to the body thereby producing a wet paint layer stack on the body; and the sensor system according to the third aspect. The painting device or a further processing unit is operationally coupled to the sensor system and configured for further processing the painted body in dependence of the obtained paint layer parameters.

The sensor assembly and method according to embodiments of the invention allow for obtaining an accurate and meaningful set of paint parameter(s), in particular a reliable thickness of a paint layer, when two or more paint layers of a coating are still wet. This is achieved by making use of a large amount of information from the detected THz radiation response of the painted body, by fitting the predicted response signal of a physical model to the detected THz response signal. The Invention opens ways to perform, for the first time, industrial quality control of wet paint layer structures by determining their individual thicknesses and properties and by reliably predicting the dry thicknesses of each wet layer after curing. The Invention can be used for on-line, in-line, at-line and off-line quality control, but is preferred to be used in-line where it is foreseen to have a significant positive impact on the shortening of the production lead time in e.g. today's automotive and aviation industry.

Further advantages, features, aspects and details that can be combined with embodiments described herein are evident from the dependent claims, the description and the drawings.

BRIEF DESCRIPTION OF THE DRAWINGS

The details will be described in the following with reference to the figures, wherein.

DETAILED DESCRIPTION

Figure 1:
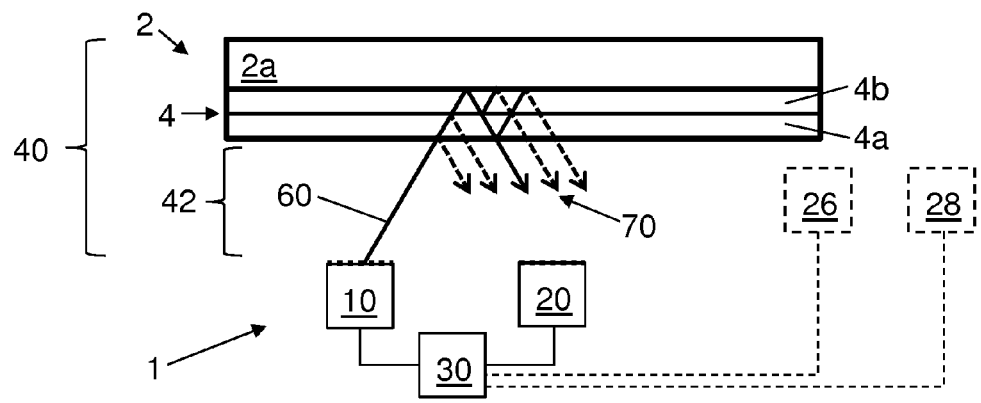
FIG. 1 is a schematic side view of a sensor system according to an embodiment of the invention.

In the following, some more aspects of the invention are described. Unless explicitly stated otherwise, the aspects are independent of each other and can be combined in any manner. For example, any aspect or embodiment described in this document can be combined with any other aspect or embodiment.

First, some general aspects are described. According to an aspect of the invention, a method for determining a current thickness of at least one wet paint layer in a stack of at least two wet paint layers, which is also called wet paint layer stack herein, is provided. Further, the method allows to determine a predicted dry paint layer thickness of at least one, several and/or all wet paint layer(s) of such a wet paint layer stack. Herein, a wet paint layer is defined as a layer that has not yet dried, and that still has a liquid, or uncured, component. This is only the case for paints that have been applied recently and for which the liquid component has not yet evaporated, or in which the chemical reaction of curing is not finished. Hence, according to an aspect, the method is carried out less than 12 hours, more typically less than 4 hours, even more typically less than 1 hour, after the paint stack has been applied. According to a further aspect, the method is carried out by a sensor system in a non-contact manner, i.e. without any sensor component requiring direct physical contact with the painted body. This does not exclude a holder holding the painted body, or any further sensor component other than the THz emitter and receiver having contact with the painted body.

As used herein, the terms "wet" and "dry" are intended to have the following defined meanings. "Wet", as used herein, is generally a status of a paint layer which lasts from its application to a substrate or another paint layer, by a machine or a human, until the paint layer has reached, after drying during a drying process, a dry status. The term "dry" may be generally defined such that at least one defined, suitably chosen physical or chemical property or parameter of the paint layer has reached a value which does not change anymore on a long time perspective—meaning that it has reached a value which would be identical if measured after, e.g., two weeks or two months. An example for an appropriate parameter in the present context is the thickness of the paint layer, which typically shrinks during the drying process and then is constant when dry. Another suitable parameter is an optical property of the paint layer, such as transmittance or reflectance, with regard to radiation of a certain wavelength, e.g. in the Terahertz range. A further suitable parameter may be the physical hardness of the paint layer. A further applicable definition for "dry" in the present context is that the first time derivative of one the above parameters has reached a predefined minimum value. Generally, the time span after which a paint layer or a paint layer stack is "dry" in the above sense varies strongly in practical application, depending on the type of paint, the applied layer thickness, the number of layers, the ambient temperature, the temperature of the substrate etc. The time for reaching a dry status may thereby vary in practical application of the methods according to embodiments from some minutes, over hours, up to some days. When it is referred herein to a "wet" status of a paint layer or stack, this is generally intended to mean that the paint layer has not reached a dry state in the above sense.

According to a further aspect, the method provides the current thickness of at least one wet paint layer irrespective of the kind of paint employed for it (e.g. of a paint type such as water-borne or solvent-borne, of kind of solvent, and/or of color). Thereby, a predicted dry paint layer thickness is typically obtained by additionally using calibration data, also called pre-stored data, containing information specific to the paint of that at least one wet paint layer of which the dry paint layer thickness shall be determined.

According to a further aspect, paint parameters further include, besides the wet layer thickness, at least one of the following (a)-(e), of the at least one wet paint layer:

(a) a paint type identifier characterizing a type of paint contained in the at least one wet paint layer, such as water-borne or solvent-borne wet paint layer. Other identifiers may include a characteristic of the absorption spectrum and/or a type of at least one of pigment, additive, and solvent. The paint type identifier is optionally obtained (possibly among others) from a parameter characterizing the frequency-dependence of the index of refraction (or of a quantity related to the index of refraction, such as a transmission index or reflection index) of the respective wet paint layer;

(b) a specific weight of the wet paint layer, wherein the specific weight of the layer is optionally obtained from at least one of the index of refraction and the paint type identifier of the layer;

(c) a defect parameter indicating a defect in the wet paint layer;

(d) a total number of paint layers including all wet paint layers in the wet paint layer stack, and optionally at least one dry paint layer between a painted substrate and the wet paint layer stack; and (e) a predicted dry paint layer thickness of at least one wet paint layer, i.e. a predicted value of the thickness which the wet paint layer will have once it has dried or cured.

According to a further aspect, a plurality of the paint parameters, and preferably all of the paint parameters, are obtained simultaneously, using a measurement from the same data source(s), the data source(s) including a THz radiation receiver.

Preferably, a single measured waveform or spectrum is used for determining the plurality of paint parameters. In other words, a plurality and preferably all of the individual wet paint layer parameters of the wet paint layer stack (and of an optional at least one dry paint layer between the substrate and the wet layer stack) are determined from a single response signal. Herein, for example each of the waveforms of FIGS. 6-9 is understood as a single measured waveform, even if each of the waveforms is generated from multiple THz pulses. A single measured waveform is understood to be a single curve of continuous time- or frequency-dependence. Normally, a single waveform as described herein contains sufficient information for determining the parameters of all wet paint layers present in the wet paint layer stack, and of as many further dry paint layers as are present (e.g., up to 8 layers in total, or more).

According to a further aspect, the method is based on an analysis of the entire response signal (essentially all data points of the detected THz radiation signal). Thus, any change of the measured response signal (e.g. time trace), at any point, influences the error function associated with a given guess for a simulated response signal, and thereby has an influence on the final result of the predicted response signal. This makes the method extremely sensitive to any information contained in the measured response signal, and allows for the determination of individual wet paint layer parameters even in the case that the optical contrast, with respect to THz radiation, between the different wet paint layers, and optionally dry paint layers, is very small.

According to an aspect, the THz emitter and THz detector are moved along a surface of the painted body, thereby generating a position-dependent thickness map of the painted body. For example, this aspect may be used for mapping the surface area of the painted body.

Next, some aspects relating to the painted body are described in more detail. According to one aspect, the wet paint layer stack is applied to at least one lower paint layer, thus forming a mixed stack of a wet paint layer stack having two or more wet paint layers, and optionally at least one dry paint layer positioned between the substrate to be coated and the wet paint layer stack, thus resulting in effect in a multi-layered paint stack. The individual layers are arranged, in thickness direction of the painted body, on top of one another, and optionally the at least one lower paint layer is dry. According to an aspect, the total number of paint layers of the multi-layered paint stack, including optional dry paint layer(s), is eight or less.

According to an aspect, the individual wet paint layers of the wet paint layer stack have a thickness—which strongly depends on the technical field to which the painted body belongs—of less than 1200 µm, or less than 600, or less than 200 µm. However, the methods according to embodiments described herein are also applicable for larger and smaller thicknesses, e.g., up to 5 mm per paint layer, or down to, e.g., 10 µm and below.

According to a further aspect, the individual dry paint layer(s) and wet paint layers of the multi-layered paint stack are one or more from the following types (a)-(e): (a) an e-coat layer; (b) a primer layer; (c) a base coat layer; and (d) a clear coat layer, (e) a mixture between any two or more of the former of (a) to (d). According to a further aspect, the multi-layered paint stack has at least two or at least three, or all of these layers (a)-(e). Also, one or more of these types may form the dry paint layer(s) located between the substrate and the wet paint layer stack. As an example, a dry paint layer on the substrate may be an e-coat layer which is dried, because it was applied to the substrate more than one day, or even longer, prior to the application of the wet paint layer stack—which might in that case, e.g., comprise wet layers from the types of a primer layer, a base coat layer, and a clear coat layer.

According to a further aspect, the painted body is one of an automobile component, a train component, an aircraft component, and a wind turbine component.

According to a further aspect, the painted body comprises at least one of a ferrous metal, a non-ferrous metal, and a fiber composite material as a substrate on which the wet paint layer is applied (optionally with other, already dried paint layers in between).

Next, some aspects relating to the algorithm for fitting the predicted response signal to the detected response signal and for finding the model parameters are described in more detail. The algorithm is based on a physical model, i.e. a function outputting a predicted response signal based on model parameters as input variables. In addition, the reference signal and possibly other data such as measured temperature, moisture, and/or other variables are input into the physical model as additional input variables. The physical model is based on physical considerations, e.g. a model describing the optical properties of the wet paint layers and physical laws describing their interaction with the THz radiation.

The model parameters may include quantities of interest such as an index of refraction or a parameterization thereof. Further details regarding the model parameters are given below.

According to an aspect, the model parameters of the physical model are determined by optimizing the model parameters such that a predicted response signal of the physical model is fitted to the detected THz response signal. The algorithm includes the following input data: a reference waveform (in time domain) or reference spectrum (in frequency domain) or some other signal sequence describing the emitted THz radiation signal not having interacted with the painted body, and the detected response having interacted with the painted body. In addition, other parameters characterizing the painted body may be inputted, such as known properties of the paint (e.g. a known parametrization of its index of refraction), known number of layers of the wet paint layer stack, known number of dry paint layers between substrate and wet paint layer stack, known thickness of some of the (dry) paint layers if available, a temperature of the painted body, etc. Likewise, other parameters characterizing the ambient medium may be inputted, such as an ambient moisture and/or a temperature. Any of these parameters can, according to a further aspect, alternatively also be obtained as input parameter which is then determined by the fitting algorithm described herein. Also, for determining a predicted dry paint layer thickness of at least one wet paint layer, optical properties of the employed paints are previously stored for application in the physical model, respectively for use in the algorithm described below. These optical properties are the index of refraction of the respective paint in a dry state, and the index of refraction in a wet state—wherein the latter is, for example, determined at a point in time which is within a time span of 0 to 30 percent of the time span which has been previously experimentally determined for this paint layer or paint layer stack to reach a dry state after application. The index of refraction in a wet state may also be determined at a later stage in the drying process, however the earlier it is determined after application of the paint, the better is typically the general accurateness of the methods herein.

Preferably, an iterative algorithm is used. The iterative algorithm includes the following steps: (a) calculating a simulated (predicted) response based on the physical model using an initial guess for the model parameters; (b) calculating an error function expressing a deviation between the predicted response signal and the detected response; (c) iterating steps (a) and (b), whereby instead of the initial guess in step (a) the model parameters are updated in order to reduce the error function. These steps (a) and (b) are iterated until the error function satisfies a best-fit criterion. Finally, (d) obtaining the fitted parameters as the final parameters satisfying the best-fit criterion in step (c). Then, at least some of the paint parameters of at least one of the wet paint layers of the wet layer stack are calculated from the fitted model parameters, typically at least one wet layer thickness, or more typically all thicknesses of the individual wet paint layers, and at least one—or all—predicted dry paint layer thickness(es) of the wet paint layer(s).

The paint parameters are thus determined by calculating a best-fit response as a function of the model parameters, such that the best-fit response satisfies a predetermined best-fit criterion for an error function expressing a deviation between the predicted response and the detected response. The best-fit criterion may include a minimization criterion for the error function.

The error function may include, e.g., the $L^2$ norm of the difference between the predicted response signal and the measured response signal. Possibly, additional terms may be added to the $L^2$ norm as described below. According to a particular aspect, the error function has a frequency dependent sensitivity. Hence, a particular difference between the frequency-domain predicted response signal and the frequency-domain measured response signal may lead to an error function whose magnitude depends on the frequency at which the difference occurs.

Once the model parameters are determined, at least some of the paint parameters are then calculated from the model parameters.

The iterative best-fit algorithm as described herein ensures a reliable analysis that takes into account the entire information contained in the detected THz radiation signal. Therefore, the result is robust even in case of very weak optical contrast between the layers, because it is based on a large number of data points (entire measured response signal). Further, this approach allows the result to be consistent with a realistic understanding of the underlying physical phenomena present in the painted body.

Next, some aspects regarding the model parameters of the physical model are described in more detail. The model parameters are indicative of optical properties of the wet paint layer describing the interaction of the THz radiation signal with the wet paint layer, and thereby allow calculation of a predicted response signal using the physical model. Also, once the best-fit model parameters are determined, the model parameters allow calculation of the paint parameters.

The model parameters may include, for example, at least one of the index of refraction, indices of transmission and reflection, and a parameterization thereof, preferably such a parameterization that allows for a frequency dependence. According to an aspect, the model parameters describe the wet paint layer as if it was a homogenous medium with respect to Terahertz radiation. This is a good approach for most wet paints.

The model parameters typically, but not necessarily, include any of the above-mentioned parameters for all of the individual layers of the paint stack, e.g. a current thickness of each layer and/or a parametrization of the index of refraction. In addition, the model parameters may include the number of layers, the type of paint applied for each layer, and the time which has passed since the application of each individual layer.

Preferably, the physical model and the model parameters enable a parameterization of the index of refraction and/or of the transmission and reflection coefficients for each layer separately in such a manner that these quantities have a frequency dependence (e.g. by describing at least one resonance contributing to the index of refraction). In an example, a frequency dependence can be obtained by expressing the transmission and/or reflection coefficients in terms of a frequency-dependent index of refraction of each layer. The frequency-dependent parameterization is preferably based on physical considerations. Preferably, the model parameters allow the index of refraction and/or of the transmission and reflection coefficients to be expressed as complex numbers, i.e. they allow a non-zero imaginary part of these quantities.

In the following, possible model parameters for parameterizing a frequency-dependent index of refraction $n(\omega)$ of one wet paint layer of the painted body, $\omega$ being frequency, are given by means of example. Namely, the functional form of $n(\omega)$ may be expressed using the following parameterization that approximates the expected frequency dependence:

$$n(\omega)^2 = n_0^2 + \Sigma_k n_k^2 * p_k(\omega) \tag{1}$$

Herein, $k=1 \ldots N$ is an index (N being a natural number, e.g. $N=1$), and $n_0$, $n_k$, are the model parameters, and $p_k(\omega)$ is a frequency dependent function that represents physical phenomena in the wet paint layer. The parameterization of equations has not only the advantage of approximating the expected form of an index of refraction of a wet paint layer well, but also allows for a physical interpretation of the frequency-dependency being caused by physically relevant modes in the wet paint layer, e.g. absorption modes.

According to a further aspect, the parameterization of the index of refraction includes a frequency-dependent contribution (e.g. the function $p_k(\omega)$ mentioned above) describing a resonance. The frequency-dependent contribution may, for example, be expressible as $$\omega_p^2 / (\omega_0^2 - \omega^2 - i\gamma\omega),$$

wherein $\omega=2\pi f$ is the angular frequency, $\omega_0$ is a peak angular frequency, $\omega_p$ is a plasma angular frequency, $\gamma$ is a damping coefficient, and i is the imaginary unit. The initial values for the resonance term above may for example be determined by looking up specific absorption spectra of the employed paint(s) and to use characteristic frequencies therefrom as parameters.

Other specific examples of a functional form of $p_k(\omega)$ are given in the detailed description below. In a variation of this example, any other parameterisation of $n(\omega)$ or some other parameter indicative of optical properties of the respective layer can be used as well.

Further model parameters are the current thicknesses, that is, at the time of the application of the THz radiation, of the paint layers, and particularly of the wet paint layers of the wet layer stack. Further possible model parameters are discussed in the description of the predicted dry paint layer thickness below.

Next, some aspects relating to the emitted THz radiation signal and the received (analyzed) THz radiation signal are described in more detail. Herein, THz radiation is defined as electromagnetic radiation of (i.e. including a non-negligible signal component having) a frequency in the range of 0.1-10 THz. The detected signal (e.g. time-domain waveform and/or frequency-domain spectrum of the detected THz radiation) is also referred to as the response signal.

The emitted/received THz radiation signal may be a continuous signal, a THz pulse or partial THz pulse. Herein, a partial pulse or partial wave is defined as partially—in amplitude—reflected or transmitted portions of the emitted pulse/wave: For example, each of the lines corresponding to portions of the response signal 70 in FIG. 3 indicates a partial pulse/wave.

Next, some aspects relating to further input data are described in more detail. According to a further aspect, the sensor system further comprises at least one of an air moisture sensor, a temperature sensor and a clock operationally coupled to the processing unit. The method may then further comprise obtaining at least one of an ambient air moisture value from the air moisture sensor, a temperature value from the temperature sensor and a time since application of the paint from the clock, and inputting the obtained value in the processing unit.

Next, some aspects relating to the geometrical arrangement of the sensor apparatus are described in more detail. According to an aspect, the emitter system and the detector system may be arranged on the same side of the painted body. This is particularly advantageous in the case that the substrate of the painted body is reflective to the THz radiation, e.g. a metal substrate of an automotive body.

Generally, it is preferred (but not required) that the emitter system and the detector system are arranged such that the THz radiation impinges on the painted body in a direction normal to its surface. For example, according to an aspect, the sensor system may comprise a semitransparent THz reflector as beam splitter. The beam splitter may be arranged at an angle with respect to the painted body sheet, such that an optical path from the emitter system and an optical path to the detector system are guided to/from a common optical path that is substantially perpendicular to the painted body. As a result, the emitter system and the detector system are arranged for respectively emitting and detecting light rays having a right angle of incidence with respect to the painted body.

Other arrangements are possible as well. For example, the emitter system and the detector system can be arranged on opposite sides of the painted body for performing a transmission measurement. This is particularly useful if the substrate of the painted body is at least partially transparent to THz radiation (e.g. transmission of at least 0.1% of the beam intensity of the THz radiation).

Next, some aspects regarding the determining of the type of wet paint layer of one or more individual layers is described as a further paint parameter(s). For this method, a reference dataset of relevant paint types is stored in the system memory of the control unit. The reference set includes, for each of the paint types, one or more optical properties such as a value or a range of a model parameter or paint parameter or a quantity derivable therefrom.

The one or more optical properties of each individual paint layer are determined during the fitting procedure and are subsequently compared to the reference dataset. The paint type is then determined as the entry from the reference dataset that is most consistent with the determined optical properties, e.g. has the least deviation from the determined optical properties or defines a range covering them. In a particular aspect, the reference dataset has been determined in the same paint line and then used as reference. For example, the reference dataset may be a parameter that has been previously obtained by characterizing a paint layer of at least one previous painted body in a wet state and/or in a dried state.

Possible kinds (types) of paint are: waterborne basecoats such as silver, mica, sky blue, solvent borne paints such as white primer, 2K blue base coat, clear coat.

Next, some aspects regarding the determining of the number of layers is described. According to an aspect, two or more wet paint layers are comprised in a wet paint layer stack, wherein optionally one or more further dry paint layers as described above are present between substrate and wet layer stack. The model parameters may further include a parameter indicating the number of layers as a further (integer-valued) fitting parameter.

Next, some aspects regarding the determining of the identification of possible defects is described. By the same method as for determining the number of layers, it is possible to identify possible defects below the wet paint layer, such as gas bubbles, instead of or in addition to the number of layers. The defect is detected as a further "layer" of low index of refraction relative to the wet paint layer. Due to the high difference in index of refraction with the surrounding paint layers, the optical contrast is high, and reliable detection of the defect is possible.

Hence, according to an aspect of the invention, a defect is detected by determining the number of layers as a function of location, and by registering a local variation in the number of layers. The defect area may then be determined as an area having an increased number of layers relative to its surrounding. Thereby, the size of the defect may be determined as the size of this area. Within this area, also the index of refraction of the defect may be determined, and therefrom optionally a type of defect may be determined.

In a further aspect, the method may also be used to identify if there is a failure with respect to the paints employed. For example, if the optical properties of the various types of paints which may be employed in the painting process are stored in the memory, Next, some aspects relating to the characterization of the wet paint layer are described in more detail. These aspects are only useful in the case of the wet paint layers, but not for paint layers that have already dried. Herein, a wet layer is a layer that has not dried yet but in which still some drying (evaporation or curing process or the like) takes place. The drying process can be considered terminated (dry paint layer) after a given time span (e.g. 1 h, 3 h, 6 h, 10 h, 20 h) has elapsed after paint application, this time span being highly dependent on a number of parameters, which was laid out further above. The time span after which a dry state has been reached may thus be experimentally determined beforehand for a given paint setup, or may also be known by experience. Measurements in the methods according to embodiments which are carried out on a wet layer or wet layer stack, may typically be carried out at a point in time within, e.g., 0 to 30 percent of the determined time span for reaching a dry state—while the overall accurateness typically rises when measurements in the wet state are carried out more early after application of the paint.

According to an aspect, a dry fraction of the wet layer defines the amount of dry components relative to the total amount (in terms of relative influence on optical properties) of the wet layer. According to an aspect, the method is carried out while the dry fraction is less than 1 and preferably while the dry fraction is less than 0.95. According to a further aspect, the model parameters (e.g. parameters parametrizing the index of refraction) related to the wet layer are such that they provide a parametrization of the optical properties of the wet layer based on a physical model that is applicable for any value of the dry fraction between 0.3 and 1. According to a particular aspect, the model parameters include a dry-fraction parameter expressing the dry fraction.

According to a further aspect, the model parameters are effective parameters describing the wet paint layer as if it was a homogenous medium with respect to THz radiation. According to a further aspect, the model parameters and the paint layer parameters are determined without use of the time passed since application of the wet paint layer.

According to a further aspect, the model parameters and/or the paint layer parameters include the current wet layer thickness for each of the at least two wet layers of the wet layer stack.

Next, some aspects relating to the dry thickness prediction, or dry paint layer thickness prediction, of a wet paint layer are described in more detail. Namely, according to an aspect of the invention, the determining step includes determining the predicted dry paint layer thickness of at least one wet paint layer of the wet layer stack.

One solution for determining the predicted dry paint layer thickness is based on a dry-fraction parameter indicative of a relative amount of a dry portion of the wet paint layer, and the determining step includes determining the predicted dry paint layer thickness as a function of the dry-fraction parameter (which does not exclude dependence on other parameters such as the current wet layer thickness). The predicted dry paint layer thickness may, for example, be determined as a product of the dry-fraction parameter and the current wet layer thickness. This type of calculation of the dry-fraction parameter is particularly useful in the framework of the Bruggeman effective medium theory. Herein, according to an aspect, the optical properties of the wet paint layer are given by an effective optical parameter $\epsilon_{eff}$ describing the optical properties of the wet paint layer as a homogenous medium. The effective optical parameter $\epsilon_{eff}$ is calculated using a wet-portion optical parameter $\epsilon_{corr}$, a dry-portion optical parameter $\epsilon_{dry}$ and a dry-fraction optical parameter f by solving Eq. (5) below for $\epsilon_{eff}$. Herein, f parametrizes a relative weight of the dry-portion optical parameter relative to the wet-portion optical parameter.

For $\epsilon_{dry}$ and $\epsilon_{corr}$ of Eq. (5), previously determined values are used. These values may, for example, have been determined by the analysis of a previously painted body in a wet state and in a dried state.

The dry-fraction parameter f of Eq. (5) is used as a model parameter, and the final value of f is obtained as the best-fit value. Then, once that f is determined, the predicted dry paint layer thickness is obtained as a function of the dry-fraction parameter.

Thereby, according to an aspect, the predicted dry paint layer thickness is determined without use of any information about the elapsed time since the paint deposition. Further, the method preferably provides the predicted dry-layer thickness by an algorithm that is independent of the kind of paint.

Another solution for determining the predicted dry paint layer thickness is based on a predetermined function stored in a memory of the controller, which outputs the predicted dry paint layer thickness as a function of prediction-relevant input parameters. The prediction-relevant parameters may include model parameters, other paint layer parameters, or parameters obtained from other sources such as a sensor and/or a clock. In particular, the prediction-relevant parameters comprise parameters describing at least one of the current thickness of the wet layer, the type of paint, and the elapsed time since the paint deposition. The prediction-relevant parameters may further contain at least one of the following: humidity; temperature; wet layer thickness at a first time; and wet layer thickness at a second time.

According to this aspect, the predicted dry paint layer thickness may be calculated using a predetermined function which relates the determined wet layer thickness and the respective elapsed time as input values to the predicted dry paint layer thickness as output value.

The predetermined function may determine the predicted dry paint layer thickness based on a stored lookup table which has been obtained from previous measurements using the same paint. Alternatively, the function may be an arithmetic function, which depends on paint-specific calibration data such as paint-specific time constants (see FIG. 10 discussed below for examples).

According to a particular aspect, the predicted dry paint layer thickness may be calculated using a predetermined function which relates a plurality of wet paint layer thicknesses determined at different elapsed times, and these elapsed times as input values to the predicted dry paint layer thickness as output value. In this case, the function may be based on an arithmetic function having at least one paint-specific parameter (e.g. a time constant), and the plurality of wet paint layer thicknesses and the associated elapsed times may be used for obtaining a best-fit of the at least one paint-specific parameter.

According to a further aspect, in case the function depends on an a priori unknown paint type parameter, this parameter may be obtained, for example, by retrieving paint-specific calibration parameters, such as the dielectric function $\epsilon_{dry}$ of the dry component and/or a stored dielectric function $\epsilon_{corr}$ of a remainder of the wet paint layer, and at least one of (a) calculating the predicted response signal by optimizing the model parameters while keeping the paint-specific calibration parameters fixed, and (b) selecting from a discrete number of paint-specific calibration parameters.

Next, some aspects relating to the method and facility for painting a body are discussed. According to an aspect, the paint is applied to the body by spraying. According to a further aspect, the wet paint layer comprises one of a water-borne paint or solvent-borne paint. According to a further aspect, the painted body is further processed in dependence of the obtained paint layer parameters. This further processing may take place while the wet paint layer is not yet dry; this allows corrective action to any imperfections before full drying of the wet paint layer. Alternatively, the further processing may take place while the paint layer has dried and is no longer a wet paint layer. The further processing may include removing the painted body from the processing line temporarily (e.g. for re-painting) or permanently. The further processing may also include removing the paint and/or applying further layer(s) of paint.

The invention is also directed to systems for performing the methods described herein. According to an aspect, the sensor system comprises an emitter system for emitting THz radiation towards the painted body; a detector system for detecting THz radiation coming from the painted body; a positioning system for positioning the emitter system and the detector system relative to the painted body; and a processing unit operationally coupled to the emitter system and the detector system. The sensor system is configured for characterizing a painted body by the method according to any aspect described herein. Herein, the term "configured for" includes that the processing unit is equipped and programmed to this effect. For this purpose, a memory of the processing unit may be equipped with program code for causing a processor of the processing unit to execute the method according to any aspect described herein.

The Invention can be used for on-line, in-line, at-line and off-line quality control, but is preferred to be used in-line where it is foreseen to have a significant economic impact on the production lead time in e.g. today's automotive industry.

DETAILED DESCRIPTION OF THE FIGURES AND OF EMBODIMENTS

Reference will now be made in detail to the various embodiments, one or more examples of which are illustrated in each figure. Each example is provided by way of explanation and is not meant as a limitation. For example, features illustrated or described as part of one embodiment can be used on or in conjunction with any other embodiment to yield yet a further embodiment. It is intended that the present disclosure includes such modifications and variations.

Within the following description of the drawings, the same reference numbers refer to the same or to similar components. Generally, only the differences with respect to the individual embodiments are described. Unless specified otherwise, the description of a part or aspect in one embodiment applies to a corresponding part or aspect in another embodiment as well.

In the following, it will be shown with respect to FIGS. 1 to 10 in section 1, how the optical properties of each layer of a paint layer stack—which may comprise at least one dry paint layer on a substrate, and at least two wet paint layers formed thereon forming a wet paint layer stack—and at least one, or all thicknesses of the individual layers of the layer stack (comprising both dry and wet paint layers) can be determined according to embodiments. Thereby, a parameterization of the index of refraction of each individual layer is employed. In embodiments, optical properties and a thickness of the individual layers, at the point in time of the measurement, are obtained in conjunction with the Fresnel equations from initially guessed parameters which determine the parameterized indices of refraction for each individual layer. Thereby, it is made use of the fact that for the above described determinations of the refraction index and current thickness of each layer according to embodiments, it is not relevant if the individual layers are dried or if they are still—at least partially—wet at the time of the measurement. Consequently, all individual layers, if dry or wet, are treated identically in the partial method described in the first section.

In a second section, it is then shown how the determined individual layer thicknesses and the indices of refraction may be used, according to embodiments, to predict a dry paint layer thickness of each of the wet paint layers of the wet paint layer stack. In the process, at least the wet paint layers—if their position in the stack is known, otherwise typically all layers—are each mathematically described and modeled by employing the Bruggemann approximation for each layer individually. Using the indices of refraction for each wet paint layer, obtained in the above described process, as input for the Bruggemann approximation, together with previously obtained data about optical properties of paints employed, both in a wet state and in a dry state as described further above, the individual, predicted dry paint layer thicknesses of the various wet paint layers may be determined with high accuracy. As used herein, the terms "predicted response signal", "predicted response", and "predicted waveform" are used interchangeably.

It shall be noted that the division of the method or process into firstly determining the current thicknesses of at least one (or all) of the individual layers of the layer stack, and its index of refraction, and to secondly calculate a predicted dry paint layer thickness of that at least one layer from that data, is chosen for reasons of better and easier understanding. In the practical realization, the two steps may be, or even might typically be, integrated into one algorithm carried out as a computer program on a computer.

Section 1—Determination of Optical Properties of Each Layer of Wet Paint Layer Stack and Determination of the Current Individual Layer Thicknesses In the following section, it is described how the individual thicknesses and optical properties of at least two wet paint layers forming a wet paint layer stack on a substrate may be determined in a method according to embodiments. This method is also applicable if one or more additional already dried layers are present between a substrate and the wet paint layer stack. However, in the example, it is assumed that only at least two wet paint layers are provided on a substrate, and it is shown how their current individual thickness at a point of time of a measurement can be determined. These results are used in further method steps according to embodiments, which are described in section 2 below, to determine an estimated dry paint layer thickness of at least one of the wet paint layers.

FIG. 1 is a schematic side view of a sensor system 1 according to an embodiment of the invention. The sensor system 1 has an emitter system 10 for emitting THz radiation, a detector system 20 for detecting THz radiation, and a processing unit 30 operationally coupled to the emitter system 10 and the detector system 20. In addition, FIG. 1 shows an optional additional sensor 26, e.g. an optional humidity measurement device and/or a positioning and/or presence sensor 28, e.g. for sensing the presence and/or location of a car body. The sensor 26 may also be operationally coupled to the processing unit 30. Herein, "operationally coupled" includes an interface of the processing unit coupled to the respective system, e.g. to the emitter system for triggering emission of THz radiation and to the detector system for receiving measurement data indicative of the response signal.

Further, a coated body 2 is arranged such that the coated body 2 is faced by the emitter system 10 and the detector system 20, with an air gap 42 between the emitter and detector systems 10, 20 on the one side and the coated body 2 on the other side. The coated body 2 has a substrate 2a and a coating. In FIG. 1, the coating is a wet paint layer stack 4 comprising two wet paint layers 4a and 4b. This number of layers is shown only by means of illustration, and the coating may have any other number of wet paint layers, e.g. three, four, five, six or seven wet paint layers.

FIG. 1 also shows the path of a THz radiation signal 60 emitted from the emitter system 10. The THz radiation signal 60 (solid line) traverses the air gap 42 and partly the coated body 2, whereupon it interacts with the coated body. A portion of the THz radiation signal, indicated by the solid line in FIG. 1, is reflected at the surface of substrate 2a and propagates back through the air gap 42 towards the detector system 20. Other portions of the radiation signal 60, indicated by the dashed lines in FIG. 1, are partially reflected at various layer interfaces of the coated body, eventually propagate back towards the THz detector system 20 (as THz response signal 70), and are detected therein. Besides these reflections, also the propagation speed of the various portions of the THz radiation is influenced by and during their interaction with the coated body 2. In this manner, the detected THz signals 70 carry detailed information about the wet paint layers 4a, 4b on the coated body 2.

Figure 3:
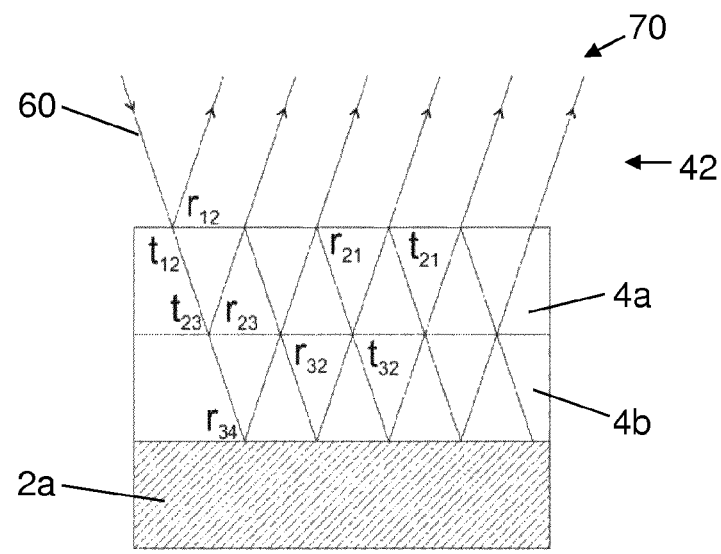
FIG. 3 is a schematic view illustrating the interaction of THz radiation emitted by a sensor system according to an embodiment of the invention with a painted body.

FIG. 3 shows the interaction of the THz radiation with the coated body 2 in more detail: At each interface of wet paint layers 4a, 4b—either with another wet paint layer or with the surrounding medium—a portion of the THz radiation is reflected, and a portion is transmitted. The reflected and transmitted portions are expressed by the complex reflection coefficients $r_{ij}$ and the complex transmission coefficients $t_{ij}$, respectively. Here, the indices ij indicate the boundaries between layers i and j, layer 4a being indicated by i,j=2, layer 4b by i,j=3 and the surrounding medium 42 by i,j=1. The reflection coefficient at the substrate 2 is written as $r_{34}$, i.e. the index j=4 refers to the reflective substrate.

The interaction of the electromagnetic radiation with this multilayer stack (air gaps 42, coated body 2 having substrate 2a and wet paint layers 4a, 4b) creates a complex pattern of reflected and transmitted signals. A portion of this THz radiation having interacted with the coated body 2 is detected by the detector system 20. This detected radiation, more precisely the set of data points representing the detected radiation (e.g. represented as a time-domain curve or as a frequency-domain curve as shown in FIGS. 6-10), is also referred to as the THz response signal 70.

The interaction of light with the multilayer structure pictured in FIG. 3 can be described by the Fresnel equations. For a thin film having two layers on a metal substrate in air (refractive index $n_1=1$), the first layer having refractive index $n_2$, thickness $d_2$ and the second layer having refractive index $n_3$, thickness $d_3$, the reflected total electric field $E_r$ can be written as a series of the partial rays:

$$E_r = E_0(r_{12} + t_{12}r_{23}t_{21}e^{-i2\beta} + t_{12}r_{23}$$
$$r_{21}r_{23}i \ldots + t_{12}r_{23}r_{34}t_{32}t_{21}e^{-i2\gamma} + t_{12}r_{23}r_{21}r_{23}$$
$$t_{21}e^{-i6\beta} + \ldots) \quad (2)$$

Herein, assuming normal incidence of the radiation, the indices of transmission and reflection $t_{ij}$ and $r_{ij}$ and the phase shifts $\beta$ and $\gamma$ can be expressed as follows:

$$t_{ij} = \frac{2n_i}{n_i + n_j} \quad r_{ij} = \frac{n_i - n_j}{n_i + n_j} \quad (3)$$

$$\beta = \frac{2\pi}{\lambda} d_2 n_2 \quad \gamma = \frac{2\pi}{\lambda}(d_2 n_2 + d_2 n_3)$$

with $\lambda$ the wavelength of the incident light, m being the (complex and possibly frequency-dependent) index of refraction, and $d_i$ being the thickness of the respective i-th layer (or air or the substrate) as described above.

The processing unit 30 (see FIG. 1) receives the response waveform (THz radiation response) 70, and also receives, or has stored therein, the waveform 60 emitted by the emitter 10. The processing unit 30 then performs an analysis of the response waveform (taking into account the original waveform 60 and other information such as detected moisture and/or temperature), and thereby obtains the coating parameters by the method described herein (see e.g. the description of FIG. 4 for additional details).

Figure 2A:
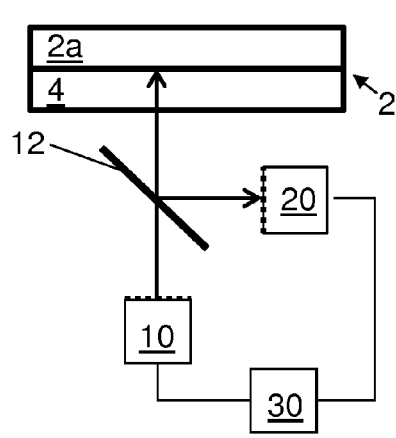
FIGS. 2a and 2b are schematic side views of possible further details and variants of the sensor system of FIG. 1.
Figure 2B:
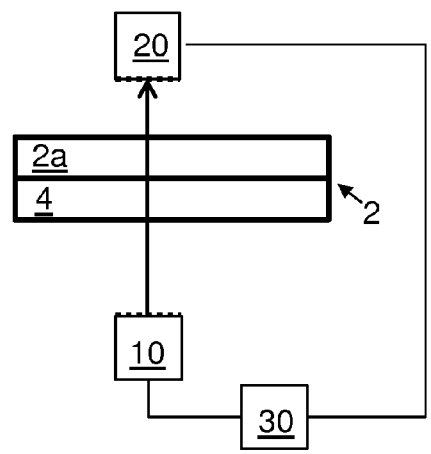

In FIGS. 1 and 3, the radiation is shown to propagate along an angle with respect to the normal direction of the coated body 2. This direction of propagation is mainly for illustration purposes, because it allows for visually separating the incoming and reflected THz radiation. In the actual setup, the main direction of propagation of the THz radiation is preferably normal to the coated body, as shown in FIGS. 2a and 2b below, so that the transmitted and received THz signals are collinear and normal to the surface of the coated body 2. In this manner, a maximum portion of the reflected signals in captured by the detector, and the reflection is minimally influenced by the geometry of the setup. Throughout the description, normal incidence is assumed, although the respective formulae can be generalized to non-normal incidence in a straightforward manner by using the Fresnel equations for non-normal incidence instead of Eq. (2).

FIGS. 2a and 2b are schematic side views of possible further details of possible implementations or variants of the sensor system of FIG. 1. In FIG. 2a, the emitter system 10 and the detector system 20 are arranged with their axes at an angle (here: 90°), and a beam splitter 12 is arranged such as to co-align the axes, so that the transmitted and received THz signals are collinear and normal to the surface of the coated body 2. This arrangement is especially advantageous in the case of the substrate 2a being reflective to THz radiation, e.g. in the case of a metal substrate.

In FIG. 2b, the emitter system 10 and the detector system 20 are arranged on opposite sides of the coated body 2 with their optical axis (direct line between them) being substantially orthogonal to the coated body 2. In this manner, a simple transmission measurement is performed instead of the measurement of the embodiment of FIG. 1. This arrangement is especially advantageous in the case of the substrate 2a being at least partially transmitting THz radiation, e.g. in the case of a resin- or polymer-containing substrate.

In the arrangements of FIGS. 1, 2a and 2b, the detector system 20 may be movable relative to at least one of the emitter system 10 and the surface of the coated body 2, e.g. movable away from a direct optical path. As described above, this allows a measurement of the surface roughness. The relative movement of the detector system 20 may alternatively or additionally be achieved by a movable emitter system and/or a movable coated body.

The resulting waveform of the THz radiation response 70 is influenced by each layer's thickness and optical properties. In particular, the amplitude of each partially reflected beam portion depends on a number of transmission and reflection coefficients, and their time separation (i.e. time difference of the partially reflected beam portion with respect to the emitted beam) depends on the optical thickness of the polymeric coating, as illustrated in FIG. 3 and described above. Hence, the full radiation response 70, together with a reference signal corresponding to the emitted THz signal 60 not having interacted with the coated body, contains sufficient information for the determination of the thickness of the polymeric coatings d2 and d3 of the wet paint layers 4a and 4b shown in FIG. 3, and of other coating parameters of the coated body.

In the following, specific aspects of the iterative algorithm for obtaining the thickness of the polymeric coating and other coating parameters are described. The inventors have found that a stable and reliable algorithm is obtained by determining the coating parameters using a physical model. Here, the coating parameters include at least one thickness of the polymeric coating of the coated body, e.g. the thickness of the coating and/or of one or more of its wet paint layer(s) and optionally also of its dry paint layers.

For definiteness, the method is illustrated for the case of a substrate 2a on which a polymeric coating consisting of two wet paint layers 4a, 4b is arranged (see FIG. 1), and for the following coating parameters to be determined:
thicknesses d2, d3 of each of the wet paint layers (the thicknesses are collectively labeled as d); and
other coating parameters that can be expressed in terms of the effective frequency-dependent index of refraction n(f) of each layer.

The discussion herein can be adapted to the case of determining a thickness of a single wet paint layer of the polymeric coating, or to the thicknesses of each of two or more wet paint layers of the coating, and of optional additional dry paint layers.

Figure 4:
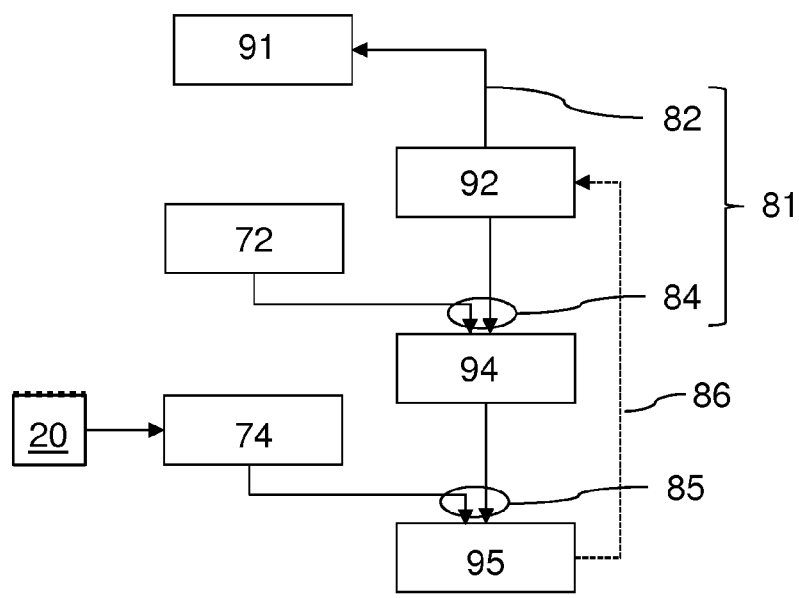
FIG. 4 is a block diagram illustrating a method of characterizing a painted body according to an embodiment of the invention.

This algorithm is illustrated in the block diagram of FIG. 4 in more detail. This algorithm is based on a physical (optical) model 81. The physical model 81 includes a waveform-prediction map 84 that maps the model parameters 92 as input to a predicted response signal 94 as output. Further, the model 81 includes a coating-parameter map 82 that maps the model parameters 92 as input to the coating parameters 91 as output. Herein, the model parameters 92 are, for example, a parameterization of the index of refraction n(f) and the thickness d for each wet paint layer; and the predicted response signal 94 is, for example, a predicted form of the response signal 70 (shown as red lines in FIGS. 5-8).

In the following, an example of the waveform-prediction map 84 is described in more detail. As stated above, the waveform-prediction map 84 takes the model parameters 92 as input and outputs a predicted response signal 94. Here, the model parameters are the thickness d for each layer (i.e. in the example thicknesses d2, d3), and a parameterization of the frequency-dependent index of refraction n(f) for each layer.

In the following, preferred aspects of the parameterization of the index of refraction n(f) are described that can be used independently of the described embodiment. The parameterization of the index of refraction is such that the index of refraction has a dependence on frequency, wherein the index of refraction preferably has the form of Eq. (1) further above. Preferably, the index of refraction includes a frequency-dependent contribution describing a resonance, and the frequency-dependent contribution is particularly preferably expressible as a function $p_k(f)$ proportional to $$\omega_{p,1}^2/(\omega_0^2-\omega^2-i\gamma_1\omega),$$

wherein $\omega$ is the frequency, $\omega_0$ is an oscillator frequency, $\omega_{p,1}$ is a plasma frequency, $\gamma_1$ is a damping coefficient, and $i$ is the imaginary unit. Alternatively or additionally, a frequency-dependent contribution may be expressible as a function $p_k(f)$ proportional to $$\omega_{p,1}^2/(-\omega^2-i\gamma_1\omega),$$

i.e. as a free oscillator having a peak at zero frequency.

Optionally there are other frequency-dependent contributions/summands, e.g. contributions from other oscillators.

For example, a possible parameterization of the (squared) index of refraction is $$n(\omega)^2 = \varepsilon(\omega) = \varepsilon_\infty + \sum_{i=1}^{n} \frac{\omega_{p,i}^2}{\omega_{0,i}^2 - \omega^2 - i\gamma_i\omega} \qquad (4)$$

where $\varepsilon_\infty$ is the dielectric constant at high frequencies, and $\omega_0$ the oscillator frequency. A (wet or dry) paint layer, as far as its interaction with THz radiation is concerned, can be expressed, for example, by at least one, but more typically by two or more oscillators: One free oscillator (for which $\omega_0=0$); and optionally other oscillator(s) being associated with different absorption bands (each with an attributed $\omega 0$, which has some finite value).

The parameterization as described above is used for each of the wet paint layers 4a, 4b. Hence, the model parameters in this case are the adjustable parameters in Eq. (4) and the thickness d for each of the layers. Thus, for example, in the case of layers each being modeled by just one oscillator representing the free (electron) oscillations of the layer (i.e. with $\omega_0=0$), the model parameters for each layer are d, $\varepsilon_\infty$, $\omega_{p,1}$ and $\gamma_1$, and the index of refraction is obtained via Eq. (4) with counter n=1 and $\omega_{0,1}^2=0$.

From the thickness d and such a parameterization of the index of refraction n(f), the transmission and/or reflection coefficients can be obtained via Fresnel equations. In the example of the coated body 2 shown in FIG. 3, the reflection and transmission coefficients $r_{ij}$, $t_{ij}$ at the interfaces of the wet paint layers 4a, 4b are, for example, given in Eq. (3) above.

The waveform-prediction map 84 further includes a set of optics equations for calculating a predicted response signal (predicted waveform for the response signal 70) 94. These optics equations may, for example, be expressed by Eq. (2) above. The optics equations have the following input parameters: (i) the waveform $E_0$ of the emitted THz radiation signal 72 (i.e. waveform of emitted radiation 60 of FIGS. 1 and 3), and (ii) the reflection and transmission coefficients ($r_{ij}$, $t_{ij}$) and the phase shifts $\beta$, $\gamma$ from Eq. (3). Other input parameters may be included as well.

The algorithm further includes an error function 85 that expresses a deviation 95 between the predicted response signal 94 on the one hand and the detected response 74 (waveform of the detected radiation 70 of FIGS. 1, 3) on the other hand. This error function 85 may, for example, be the $L^2$ norm or some other norm as described herein.

Possibly, according to a general aspect of the error function independently of this embodiment, the error function may, include a "penalty term" that penalizes a physically implausible predicted response signal; and/or a frequency-dependent term that gives additional weight to deviations in a particularly sensitive frequency range. Such a sensitive frequency range may include the frequency range between 0.1 THz and 1 THz at least partially. Such a term may, for example, be added to other contributions such as the $L^2$ norm.

According to a particular aspect, the error function has a frequency dependent sensitivity. Hence, a particular difference between the frequency-domain predicted response signal and the frequency-domain measured response signal may lead to an error function whose magnitude depends on the frequency at which the difference occurs.

Next, the coating-parameter map 82 is described in more detail. As stated above, the coating-parameter map 82 calculates, from the model parameters 92, the coating parameters 91 as output. In the example described above, some coating parameters of the coated body may be obtained from the above parameterization of n(f) as follows:

(a) A paint type identifier characterizing a type of paint may be determined from the parameters parametrizing n(ω), e.g. the parameters on the right side of Eq. (4). These values are then matched to a table in which the values or ranges of these parameters for each paint type employed are defined, and the paint type is determined based on the matching. Alternatively, only a set of discrete parameters parametrizing n(ω) may be used as input parameters of the fitting algorithm, each set of parameters corresponding to a known paint type. The set minimizing the error function is then used, and the paint type is determined as the paint type corresponding to the chosen set.

(b) A specific weight of at least one layer of the coating may be directly derived from the paint type identifier of the layer, or may be obtained in a manner analogous to the method discussed in (a) above. Alternatively, for some paints the specific weight may be expressed as a function or functional of the index of refraction, e.g. its value at a particular frequency (such as ω=0) or its integral or L2 norm over a frequency range. The function or functional may also depend on the paint type described above.

(c) a defect parameter indicating a defect in at least one layer of the coating. This defect parameter may be obtained from an abrupt local change in n with respect to its value in neighboring regions of the coating.

In addition or alternatively, the defect parameter may also be obtained by detecting the presence of an additional layer (e.g. air layer) within the coating at a particular region. According to this aspect, the number of layers is used as a fitting parameter, and a region in which the additional layer is obtained is marked as having a defect.

The thickness d was already used as a fit parameter and is identically used as coating parameter. Likewise, the number of layers N may be used as a (discrete) fitting parameter which is then identically used as a coating parameter.

Next, the iterative algorithm itself, as illustrated in FIG. 4, is described in more detail. In a first step, initial fit parameters 92 are generated, e.g. as random numbers or plausible initial values. In this example, as stated above, the fit parameters are given by the respective thickness and parameters characterizing the respective index of refraction of each layer.

Then, the initial fit parameters 92 are input, together with the reference waveform 72, into the waveform-prediction map 84; and the waveform-prediction map 84 calculates the predicted (simulated) response signal 94 using this input. Namely, the indices of reflection and transmission and phase shifts are calculated via the Fresnel equations, Eq. (3), and the predicted response signal 94 is calculated based on these coefficients using the optics equations, Eq. (2), as described above.

Then, the deviation 95 between the predicted response signal 94 and the measured response 74 is calculated using the error function 85. Then the model parameters 92 are varied depending on the coefficients and error function 85 of previous steps. This variation is performed using a strategy that eventually approaches a minimum deviation. For example, a minimization algorithm based on the Levenberg-Marquardt technique can be used. Then, the algorithm is repeated (arrow 86), now using the varied model parameters 92 instead of the initial parameters.

In this manner, the model parameters (herein also: fit parameters) 92 are varied repeatedly in the loop represented by the arrow 86, until the deviation 95 satisfies a best-fit criterion (e.g. until the deviation is sufficiently minimized or until some other cut-off criterion is met).

Then, the final fit parameters 92 of the last step are used for calculating the coating parameters 91 (e.g. thicknesses $d_2$, $d_3$) via the coating-parameter map 82 as described above.

In this manner, the coating parameters 91 are determined by calculating a best-fit response that sufficiently minimizes the deviation 95, i.e. such that the predicted response signal 94 of the physical model fits to the detected response 74. Since the algorithm takes into account the full waveform of the detected response 74 via the error function 85, and not just individual land-mark features, the result is stable and reliable by the fact that one accounts for each individual frequency component in the appropriate way, given by the physical model.

In alternative embodiments, the frequency-dependent index of refraction n(f) may alternatively also be replaced by another equivalent parameterization, e.g. the conductivity which is proportional to the index of refraction squared multiplied by frequency. Alternatively, also some other parameterization of the optically relevant properties of each layer can be used as fit parameters. For example, in a variation, the coating parameters 91 can be used directly as fit parameters. In another variation, the iterative method can be adapted to more than two layers. To this purpose, Eq (2-3) is to be generalized to more than 2 layers, which is straightforward textbook knowledge. In another variation, additional input parameters may be used (e.g. the index of refraction of the surrounding medium, e.g. air, 42, 44).

In another variation, some parameters described as fitting parameters may be determined using additional sensors or input means. Thus, for example the thickness d2 of the first wet layer 4a may be manually input if known, and the iterative method described herein may be used only for obtaining the thickness d3 of an additionally applied wet paint layer 4b.

Section 2—Predicting the Dry Paint Layer Thickness of one Single Wet Paint Layer on Top of a Layer Stack In section 1 above, a method for determining current (wet or dry) thicknesses and individual indices of refraction in a multilayer structure was described according to embodiments, wherein the multilayer structure comprises at least two wet paint layers, and optionally further dry paint layer(s) between the substrate and the wet paint layers. In the following, it will be shown how, based on the above described method steps, a predicted dry paint layer thickness of one wet paint layer 4a may be determined according to embodiments.

First, the determination of the paint parameter of a predicted dry paint layer thickness is described in principle for a single wet paint layer, which method is then in the next section transformed to be applicable to each layer of a wet paint layer stack having two or more wet paint layers, which is then employed in embodiments. The paint parameter allows reliably predicting the dry thickness of a wet paint layer on a multilayer stack after drying (e.g. evaporation and/or curing), when the THz measurement of the wet paint layer is performed at an arbitrary moment in any wet state between wet and dry.

An important general aspect of all states of paint during drying is that, when probed with THz radiation, the wavelength of the radiation is always larger than the smallest domain size. For this reason, the wet paint in each stage can be considered as being homogeneous. The inventor has found that for this reason the wet paint layer can be considered as an effective homogenous medium. This allows using the methods described in the following.

There are a number of possible approaches for predicting the dry paint layer thickness, each of which can be used with any embodiment described herein. A first approach is based on an effective medium theory in the Bruggeman approximation. Within this approximation, the refractive index n, or equivalently the dielectric function $\epsilon_{eff}$ describing the interaction of the medium with the THz radiation, is obtained from the THz data by the best-fit algorithm described above. To this purpose, within the Bruggeman approximation $\epsilon_{eff}$ (and thereby the refractive index) is parameterized by the dry-volume fraction parameter f for spherical inclusions:

$$f \frac{\varepsilon_{dry} - \varepsilon_{eff}}{\varepsilon_{dry} + 2\varepsilon_{eff}} + (1-f) \frac{\varepsilon_{corr} - \varepsilon_{eff}}{\varepsilon_{corr} + 2\varepsilon_{eff}} = 0 \quad (5)$$

Here, $\epsilon_{dry}$ is the frequency dependent dielectric function in the dry state, $\epsilon_{eff}$ is the present frequency dependent dielectric function of the wet paint layer, f is the dry volume fraction ($0 \leq f \leq 1$), and $\epsilon_{corr}$ is a frequency dependent dielectric function which represents the optical difference between the wet state and the dry state but which is independent of f. It shall be noted that $\epsilon_{eff}$ is the dielectric function of each wet paint layer which is obtained by applying the method described in section 1 above. It is noted that this model does not necessarily reflect the exact processes in drying paint, but has shown to yield good results.

The physical considerations underlying Eq. (5) are as follows: In the wet state, the wet paint layer has optically to be seen as being composed of a host material with inclusions of dry material. The volume fraction of the latter is nonzero and well below 1. With increasing drying time, the inclusions increase in volume fraction and eventually when the paint is dry, they determine the entire system (f=1). Any state in between the wet and dry state can be described by the above equation with 0<f<1.

Eq. (5) is a special case in which, e.g., spherical inclusions are assumed. More generalized variations of eq. (5) may be used instead, if appropriate. Further details on the Bruggeman approximation can be found in D. A. G. Bruggeman, "Berechnung verschiedener physikalischer Konstanten von heterogenen Substanzen", Ann. Phys. 24, 636-679(1935).

The above equation (5) allows obtaining $\epsilon_{eff}$ (e.g. numerically) as a function of f when the other parameters are known. For the present algorithm, $\epsilon_{eff}$ can be obtained from the THz data, and the parameters $\epsilon_{dry}$, $\epsilon_{corr}$ may be retrieved as paint-specific data from a memory of the processing unit in dependence of the known paint type. In particular, f can be used as a model parameter whose value is chosen such that the resulting value of $\epsilon_{eff}$ from Eq. (5) results in a best-fit of the predicted response signal to the detected response signal.

Thus, the dry-volume fraction parameter f is available as a model parameter which parametrizes the refractive index as described above via Eq. (5). The value of f, as well as the value of the other model parameters such as the wet paint layer thickness d, is then determined from the THz measurement by the best-fit algorithm described herein.

The predicted thickness of the dry paint layer, ddry, is simply given by the product of the former two, $$d_{dry} = f \times d \quad (6)$$

This method can be carried out at any time in the drying process, and the time between finishing the paint deposition and the measurement does not need to be known. The method works not only for a single wet paint layer directly on a substrate, but also for a wet paint layer on top of one or multiple dry paint layers.

The paint-specific parameters $\epsilon_{dry}$, $\epsilon_{corr}$ can be obtained by a previous calibration measurement for the given type of paint: For example, a dry state measurement is performed which gives the dry-state values $\epsilon_{dry}$ and ddry; then a wet state measurement gives $\epsilon_{eff}$ and d at some (arbitrary) moment during the drying process. With this information, Eq. (6) can then be solved for f at this moment, and then Eq. (5) can be solved for $\epsilon_{corr}$. Then, the obtained parameters $\epsilon_{dry}$, $\epsilon_{corr}$ for this paint type are stored in memory to be retrieved later as described above.

In a second approach, the predicted dry thickness of a wet multilayer paint may also be determined using stored information of the drying process. Namely, the drying behavior of each specific kind of paint as a function of a variable, which can include time (herein understood as elapsed time after paint deposition) and/or temperature and/or humidity, is known and may be stored and used as calibration data. The calibration data can for instance be the wet thickness dcal(t) of a calibration paint layer as a function of elapsed time t at a given humidity and temperature, which for sufficiently long times converges towards the dry thickness dcal($\infty$) of the calibration paint layer.

With this approach, the wet thickness $d_{wet}$ of an individual wet paint layer is obtained from the THz response signal by fitting to a physical model as described above. Given the elapsed time $t_0$ between the paint deposition and the measurement of the wet thickness $d_{wet}$, and optionally other parameters such as temperature and/or humidity (for selecting the correct calibration curve), the dry thickness ddry can be obtained from the stored calibration curve(s), for example, as follows:

$$ddry = (d_0/dcal(t_0)) * dcal(\infty)$$

In practice, the value of dcal ($\infty$) is given by the thickness of the calibration layer at large times, say, after 1 hour.

The calibration function dcal(t) can be obtained from a large table of calibration measurements previously performed for the same paint. Since a table always has a limited number of discrete entries, the actual value of dcal(t) may be obtained by interpolation between proximate entries of the table. In this manner, also a dependence on other variables such as humidity etc. can be obtained. Alternatively, an analytical form of dcal(t) can be chosen based on a physical model, such as dcal(t)=dcal $\infty$+A*exp($-t/\tau$) with fitting parameters dcal $\infty$, A and $\tau$. The exact form of dcal (e.g., exponential, double exponential or hyperbolic) may depend on the physical model appropriate for the specific kind of paint and may be more complex than this example. Then, the calibration measurement consists in finding best-fit values for the fitting parameters (in this example, dcal$\infty$, A and $\tau$) for the given paint at the given conditions.

The accuracy could be improved by performing the measurement at two or more different times t1 and t2. This will provide two thicknesses of the same measurement point at two different drying stages, and thereby two predicted dry thicknesses which can, for example, be averaged for obtaining a more reliable predicted thickness.

A third approach is similar to the second approach with analytical calibration function, but instead of (or in addition to) a previous calibration step, all or some of the fitting parameters of dcal are determined from the presently measured data. Hence, in the third approach a fitting function dfit(t, X) having a predefined behavior, e.g., exponential, double exponential or hyperbolic, is used for approximating the actual time evolution of the thickness. The functional form of dfit, as well as some or all of the time constants, are predetermined by the type of paint. Nevertheless, there remain some undetermined fitting parameters X. Then, at least two measurements dwet1, . . . , dwetN at different times t1, . . . , tN (N≥2) are used for determining the remaining fitting parameter(s) X and, thereby, the predicted dry thickness ddry=dfit(∞,X).

In this third approach, the times t1, t2 do not necessarily need to be the times since paint application, but the zero-time point can be arbitrary. In this case, the time of paint application can be one of the fitting parameters.

In the third approach, as in the other approaches, external environmental conditions such as temperature and/or humidity may optionally also be taken into account in the calibration function. Alternatively, the calibration function is valid for an average temperature and humidity, and still produces reasonably accurate results if the conditions are allowed to change to a certain extent from the specified condition.

Section 3—Predicting the Dry Paint Layer Thickness of Each Wet Paint Layer in a Wet Layer Stack In section 2, it was shown how the dry thickness of a single wet paint layer may be predicted by using the Bruggeman approximation. The inventor has found that the Bruggeman approximation may be extended to be applied to each wet paint layer of a wet layer stack individually, provided that one needs to know (and thus needs to determine beforehand) for each paint layer independently (i) the wet optical properties with respect to an index of refraction and (ii) the dry optical properties with respect to an index of refraction. Once these are known, the Bruggeman description of ∈eff of each individual wet layer given by equation (5) above may be determined by knowing ∈dry and ∈corr of each layer.

Figure 5:
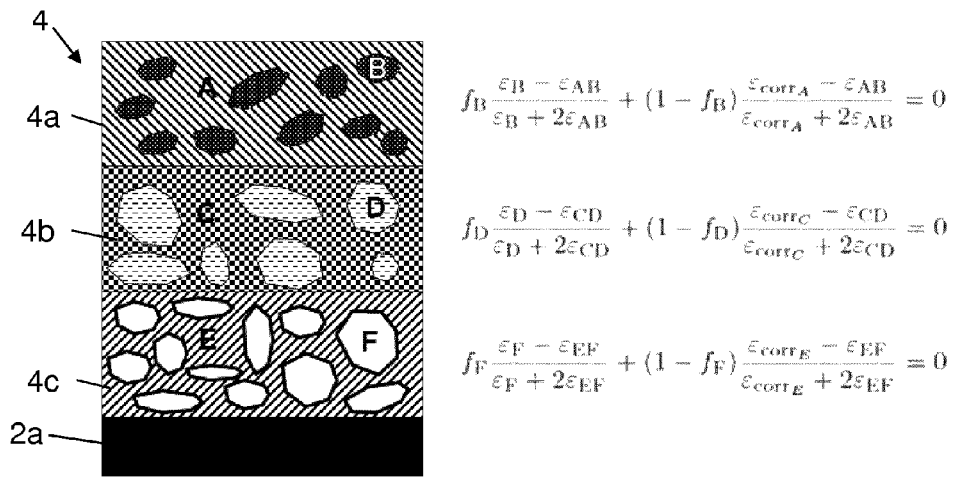
FIG. 5 shows a model of a wet layer stack on a substrate as employed in embodiments.

Subsequently, the interaction of Terahertz radiation with the wet layer stack 4 is described by formulas (2) and (3) above, wherein the index of refraction ($n_i$=SQR ∈eff) of each layer is provided by the respective Bruggeman approximation (5), as is shown in FIG. 5 on the right for a wet paint layer stack 4, comprising three wet paint layers 4a, 4b, 4c, on a substrate 2a. Thereby, ∈eff from eq. (5) is obtained from the THz data as ∈AB, ∈CD, and ∈EF, respectively, for each layer, as well as fB, fD, and fF. The parameters ∈dry are represented by ∈B, ∈D, ∈F, respectively, and ∈corr is represented by ∈corrA, ∈corrC, and ∈corrE, respectively, which values can be retrieved as paint-specific data from a memory of the processing unit in dependence of the respective paint type for each layer 4a, 4b, 4c. A proof of principle will be given below to show the feasibility. In FIG. 5, it is assumed that the bottom layer 4c with wet regions E and dry regions F is deposited at first on the substrate 2a (black) and thus is the least wet (has the highest volume fraction of dry regions F versus wet regions E), and that the top layer 4a (wet regions A and dry regions B) is sprayed latest and thus is the wettest of the applied three wet layers 4a, 4b, 4c.

Now an example or proof-of-principle of the method according to embodiments is shown. Experimental data on wet paint are used to simulate a wet multilayer stack 4 (as described for three wet paint layers 4a, 4b, 4c with respect to FIG. 5) and is subsequently analyzed using the method of embodiments of the invention in order to show the applicability of the method.

It might be assumed that, although it has been shown above that it is theoretically possible to have several wet layers using the Bruggeman approximation, which was described above as a series of layers and respective equations, such as shown in FIG. 5, the experimental data might not contain enough contrast (and thus information) to determine the two typical parameters of each wet layer, namely effective index of refraction ∈eff and wet layer thickness dwet—because the entire system of equations including the Fresnel equations, the parameterization of the refraction index, and the Bruggemann approximations could be regarded to be kind of underdetermined in a mathematical sense. However, as is shown in the following, the contrast of each paint layer is usually sufficiently large such that also experimentally, the proposed method according to embodiments yields reliable results.

Figure 6:
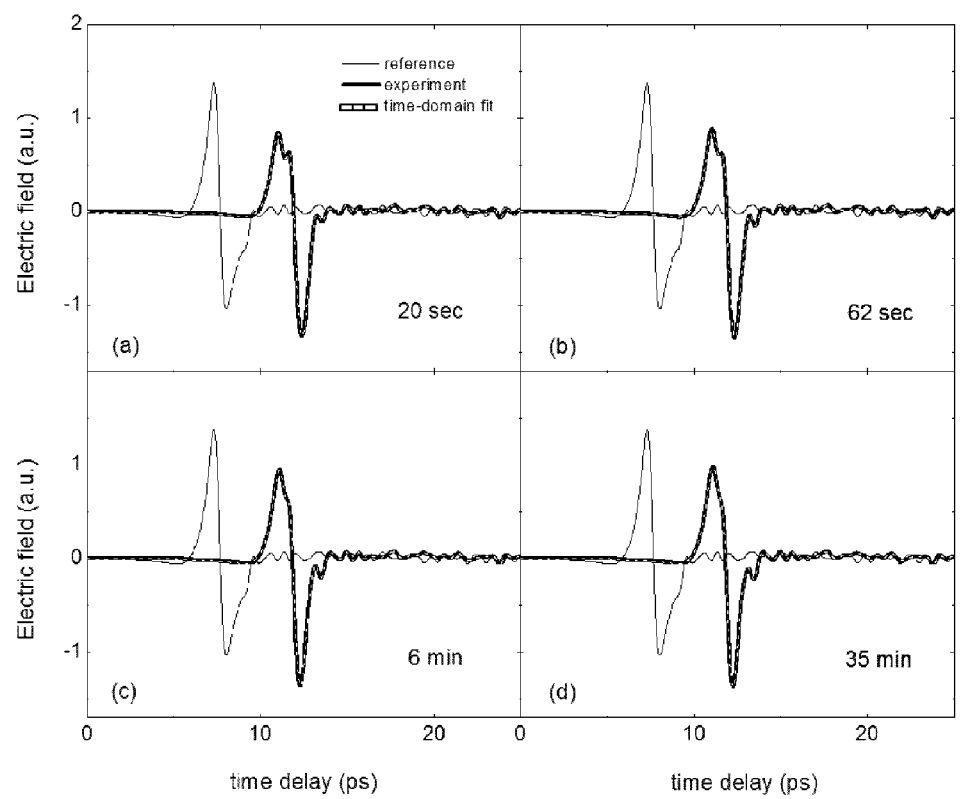
FIG. 6 is a set of four diagrams representing the response signals and related quantities of a painted body, measured by a system as shown in FIG. 1 in time domain.

The non-limiting example shown below is the case of a (waterborne) silver base coat on a primer on a steel substrate. As a prerequisite, in FIG. 6 is shown the experimentally measured reflected electric field Er(t) of a single wet primer layer on a steel substrate at various times after paint spraying, at a temperature of 40° C. to promote the drying process. The fits are based on the effective medium approach for a single wet layer as described in section 2.

Figure 7:
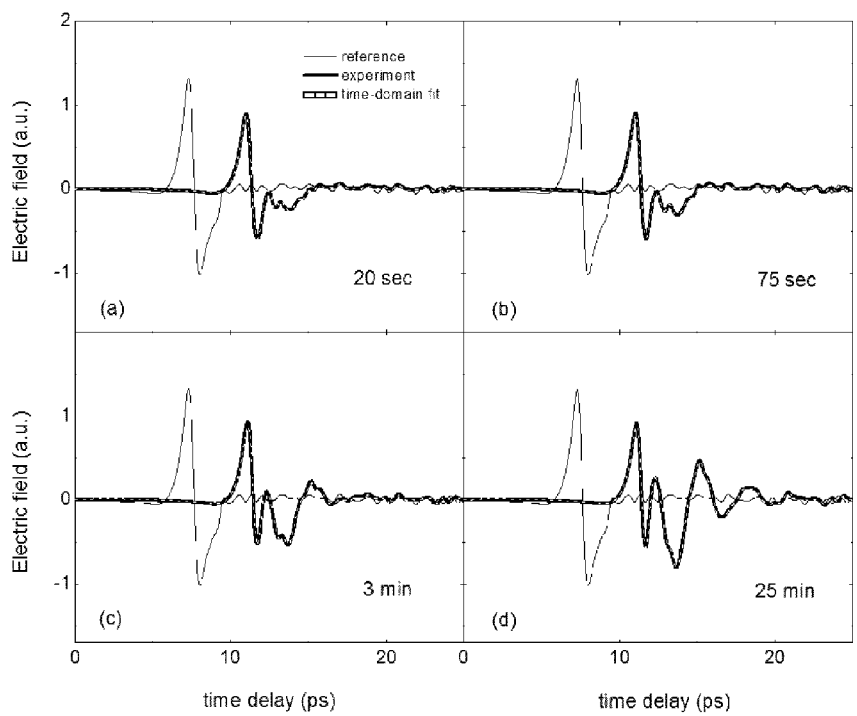
FIG. 7-9 are sets of four diagrams representing the response signals and related quantities of different painted bodies, each at four different times.

FIG. 7 shows $E_r(t)$ for a wet, waterborne silver base coat layer applied on a dry primer on a steel substrate. Whereas $E_r(t)$ of the primer almost does not change during the drying process, $E_r(t)$ of the base coat layer shows large differences between wet and dry. The fits which are also shown in all panels of both figures are based on the Bruggeman approximation of a single wet paint layer as described in section 2 above. The wet silver basecoat is 35 μm thick and deposited on dry white primer on a steel substrate. The fits are based on the effective medium approach for a single wet layer on a dry paint layer.

Figure 8:
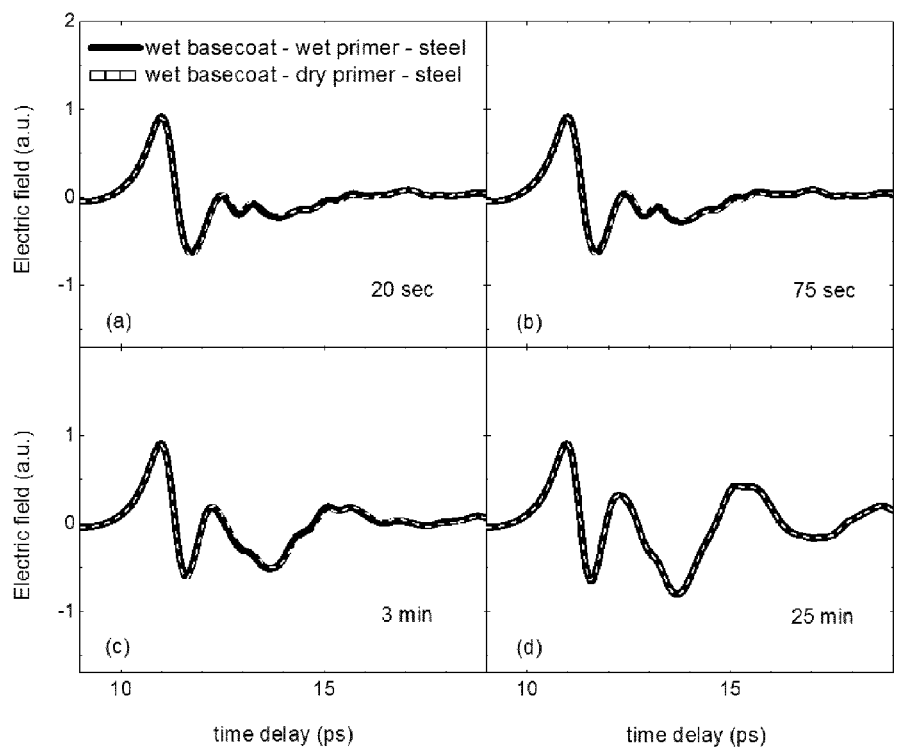

Next, the primer layer of FIG. 7 is modified to be wet instead of dry like it was in the example of FIG. 7. Measurements on the resulting wet multilayer are shown in FIG. 8. A wet silver basecoat was deposited 60 seconds after a wet primer had been sprayed on top of a steel substrate heated to 40° C., wherein 60 s at 409° C. compares roughly to 10 min drying time at room temperature. The main difference between the curves of FIG. 8a to 8c is mainly caused by the thickness change of the primer layer. The wet primer layer at deposition is about 48 μm thick, whereas the dried primer layer is only 40 μm thick. FIG. 8d does not show any difference between the curves since on a time scale of 25 min the 60 seconds difference is negligible. It is noted that in FIGS. 6, 7 and 9, the time-domain fits are almost identical to the experimental data, thus the respective two graphs seem nearly identical in most diagrams.

Figure 9:
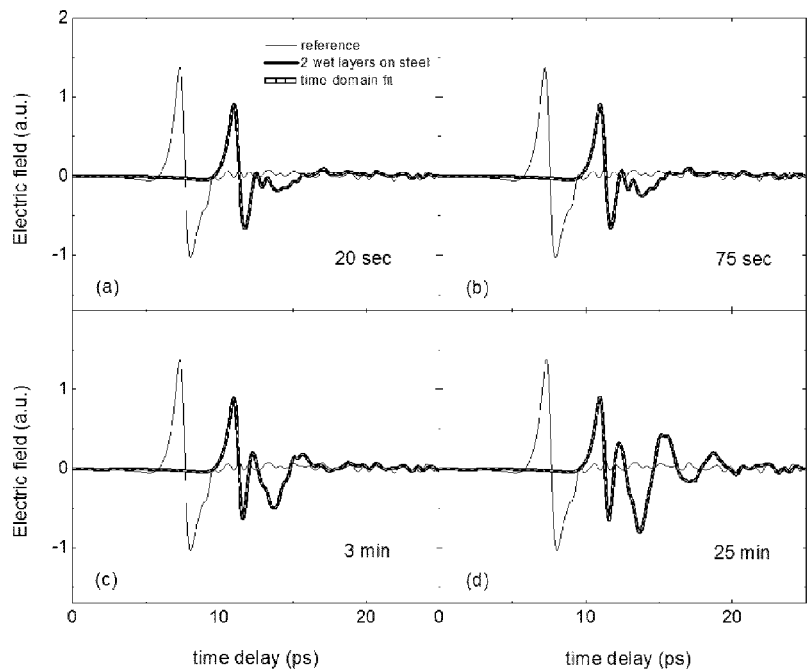

FIG. 9 shows the method of the invention based on the Bruggeman approximation for a wet bilayer, as described earlier, applied to the data of a wet basecoat on a wet primer on steel as shown in FIG. 8. The fits describe the data to high accuracy, which proves the method and which demonstrates that the reflected time-domain traces of wet multilayers contain sufficient contrast to perfectly characterize the individual wet layer properties.

Figure 10:
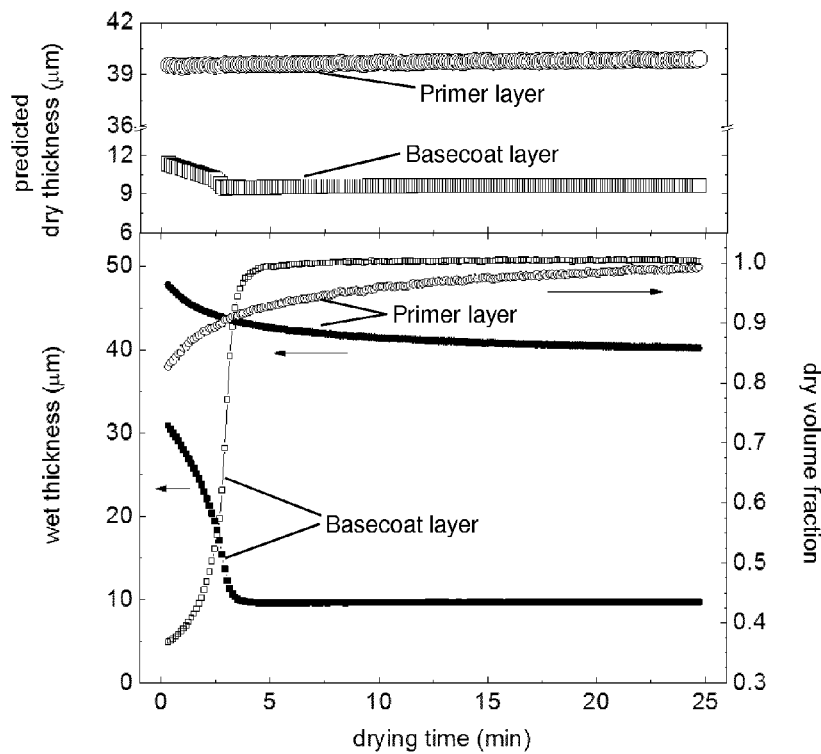
FIG. 10 is a diagram representing the wet thickness and the predicted dry thickness of various wet paint layers as a function of drying time, wherein the wet thicknesses converge to the predicted dry paint layer thicknesses with growing time after application of the paint layers.

FIG. 10 shows the dry volume fraction f (lower part of diagram, two graphs approaching value 1,0, marked with arrow to the right) and the wet thickness dwet (lower part of diagram, two graphs marked with arrows to the left) of both the drying primer layer and base coat layer as a function of drying time after deposition of the base coat, as obtained from the method according to embodiments. Similarly as for a single wet layer, the product of the dry volume fraction (filling fraction) f and the wet layer thickness dwet is basically constant during the drying time, and provides the predicted dry paint layer thickness for each individual wet layer of the wet multilayer. This is shown in the upper part of the diagram in FIG. 10, which shows the predicted dry thickness ddry.

There are many variants how the described methods may be realized by respective algorithms, of which two shall be briefly shown. With respect to FIG. 4, it was described how an algorithm as illustrated in the block diagram of FIG. 4 works in detail. The algorithm is based on a physical (optical) model 81. The physical model 81 includes a waveform-prediction map 84 that maps the model parameters 92 as input to a predicted waveform (predicted response signal 94) as output. Further, the model 81 includes a coating-parameter map 82 that maps the model parameters 92 as input to the coating parameters 91 as output. Herein, the model parameters 92 are, for example, a parameterization of the index of refraction n(f) and the thickness d for each wet layer; and the predicted response signal 94 is, for example, a predicted form of the response signal 70 (shown as red lines in FIGS. 6-9). Thereby, it was previously shown that the waveform-prediction map 84 takes the model parameters 92 as input and outputs a predicted response signal 94. Now, for determining a dry paint layer thickness of a wet layer stack, the model parameters are the thickness d for each layer (i.e. in the example of FIG. 1 thicknesses d2, d3), and a parameterization of the frequency-dependent index of refraction n(f) for each paint layer. In section 2, it was shown that for calculating the dry fraction f from the Bruggemann approximation, the values of the parameters $\in_{dry}$, $\in_{corr}$ are additionally needed as input to the algorithm, which may be retrieved as paint-specific data from a memory of the processing unit, for example—optionally in dependence of the known paint type for each layer. In particular, f can be used as a model parameter whose value is chosen such that the resulting value of $\in$eff from Eq. (5) results in a best-fit of the predicted response signal to the detected response signal.

The methods for predicting $d_{dry}$ discussed herein are remarkably reliable. Previously, in the absence of the THz measurement and data analysis as described herein, it would have been believed that the behavior of paint is too complex for predicting ddry reliably based on the limited available data. This is also because, depending on the kind of wet paint layer, many different processes may occur during the drying. Among these are chemical reactions between constituents, simple evaporation and cross-linking processes (polymerization). These processes were believed to each require a very sophisticated model in order to predict the dry state thickness. In contrast, by identifying models that capture the essential aspects of the drying process, as well as by using a method that obtains sufficient data of the paint, these difficulties could be overcome.

The methods according to the invention are especially applicable in the case that the polymeric coating is a paint film having one or more layers of paint. One use of the method and system is for the analysis of a painted automobile body or a painted automobile component. Another use is for the analysis of a train body/component, an aircraft body/component such as an aircraft fuselage, aircraft wing, or the like. Another use is for the analysis of a wind turbine component, in particular of a painted blade of a wind turbine. The substrate body may comprise at least one of a ferrous metal, a non-ferrous metal, and a fiber composite material. For example, an application of the present aspect of the invention is defect detection in blades of wind turbines e.g. for off-shore purposes. Here, the coated body is a wind turbine blade containing a defect below the paint.

While the foregoing is directed to embodiments, other and further embodiments may be devised without departing from the basic scope determined by the claims.

The invention claimed is:

1. A method of characterizing a wet paint layer stack of a painted body, comprising at least two wet paint layers, by individual wet paint layer parameters, based on fitting to a physical model,
    the method being carried out by a sensor system in a non-contact manner, the sensor system comprising an emitter system for emitting THz radiation, a detector system for detecting THz radiation, and a processing unit operationally coupled to the emitter system and the detector system,
    the method comprising:
    emitting, by the emitter system, a THz radiation signal towards the painted body such that the THz radiation interacts with the wet paint layer stack,
    detecting, by the detector system, a response signal being the THz radiation signal having interacted with the wet paint layer stack;
    determining model parameters of the physical model by optimizing the model parameters such that a predicted response signal of the physical model, which approximates the interaction of the THz radiation signal with the wet paint layer stack, is fitted to the detected response signal, wherein at least some of the model parameters are indicative of individual optical properties of the wet paint layers and of a wet paint layer thickness; and
    determining, from the determined model parameters, the individual paint layer parameters of at least one of the wet paint layers, including at least one predicted dry paint layer thickness.

2. The method according to claim 1, wherein the predicted response signal of the physical model is fitted to the detected response signal by an iterative procedure including a best-fit algorithm.

3. The method according to claim 2, comprising the steps:
    (a) calculating the predicted response signal based on the physical model using an initial guess for the model parameters;
    (b) calculating an error function expressing a deviation between the predicted response signal and the detected response signal;
    (c) iterating steps and, whereby the model parameters are varied until the error function satisfies a best-fit criterion,
    (d) obtaining fitted parameters as the final parameters satisfying the best-fit criterion in step, and calculating at least one of the wet paint layer parameters from the fitted parameters.

4. The method according to claim 1, comprising the steps:
    (a) calculating the predicted response signal based on the physical model using an initial guess for the model parameters;
    (b) calculating an error function expressing a deviation between the predicted response signal and the detected response signal;
    (c) iterating steps (a) and (b), whereby the model parameters are varied until the error function satisfies a best-fit criterion, (d) obtaining fitted parameters as the final parameters satisfying the best-fit criterion in step (c), and calculating at least one of the wet paint layer parameters from the fitted parameters.

5. The method of any of claim 1, wherein at least one of the determined wet paint layer parameters of one of the wet paint layers includes the thickness of that wet paint layer.

6. The method according to claim 1, wherein the model parameters and/or the individual wet paint layer parameters include a current wet layer thickness, and wherein the determining step includes determining the predicted dry paint layer thickness as a function of the current wet paint layer thickness.

7. The method according to claim 1, wherein the model parameters and the individual paint layer parameters are determined without use of a time passed since application of the paint.

8. The method according to claim 1, wherein at least a part of the model parameters are effective parameters describing physical properties of each of the at least two wet paint layers.

9. The method according to claim 8, wherein the individual optical properties of each wet paint layer are represented by an effective optical parameter ($\in$eff) describing the optical properties of the respective wet paint layer, wherein the effective optical parameter ($\in_{\mathit{eff}}$) of each wet paint layer is calculated as an initial guess function to which the model parameters are fitted, in the step of determining the model parameters, from a respective pre-stored wet-portion optical parameter ($\in_{corr}$), a respective pre-stored dry-portion optical parameter ($\in_{dry}$) and a dry-fraction parameter parametrizing a relative fraction of the dry-portion optical parameter relative to the wet-portion optical parameter of the respective wet paint layer, wherein the dry-portion optical parameters are part of the model parameters, and wherein the determining of the wet paint layer parameters for a specific wet paint layer includes determining the predicted dry paint layer thickness as a function of the individual dry-fraction parameter for the specific wet paint layer.

10. The method according to claim 9, wherein the pre-stored wet-portion optical parameter ($\in_{corr}$) and the pre-stored dry-portion optical parameter ($\in_{dry}$) have been previously obtained, for each paint type employed for the wet paint layers, by characterizing paint layers of at least one previous painted body in an at least partially wet state and in a dried state.

11. The method according to claim 1, wherein the predicted dry paint layer thickness is calculated based on at least one determined wet layer thickness, wherein the calculation is performed via a predetermined function relating the at least one determined wet layer thickness and the respective elapsed time to the predicted dry paint layer thickness, the predetermined function being a paint-type specific function and/or having at least one pre-stored paint-type specific parameter.

12. The method according to claim 1, wherein the painted body further comprises a dry paint layer below the wet paint layer stack.

13. The method according to claim 1, wherein all of the paint layer parameters are determined from a single THz response signal.

14. The method according to claim 1, wherein the painted body is one of an automobile component, a train component, an aircraft component, or a wind turbine component, and wherein the painted body comprises at least one of a ferrous metal, a non-ferrous metal, or a fiber composite material as a substrate.

15. A method of painting a body, the method including
applying at least two wet paint layers to the body, thereby producing a wet paint layer stack on the body;
characterizing the wet paint layer stack by the method according to claim 1, thereby obtaining the paint layer parameters including a predicted dry paint layer thickness of one of the wet paint layers and/or of the wet paint layer stack;
further processing the painted body in dependence of the obtained paint layer parameters.

16. A sensor system for characterizing a wet paint layer stack on a painted body, the sensor system comprising:
an emitter system for emitting THz radiation towards the painted body;
a detector system for detecting THz radiation coming from the painted body;
a positioning system for positioning the emitter system and the detector system relative to the painted body; and
a processing unit operationally coupled to the emitter system and the detector system,
wherein the sensor system is configured for characterizing the painted body by the method according to claim 1.

17. A painting facility for painting a body, the painting facility including:
a painting device for applying paint to the body thereby producing a wet paint layer stack on the body; and
a sensor system according to claim 16, wherein the painting device or a further processing unit is operationally coupled to the sensor system and configured for further processing the painted body in dependence of the obtained paint layer parameters.

* * * * *

UNITED STATES PATENT AND TRADEMARK OFFICE
CERTIFICATE OF CORRECTION

PATENT NO. : 10,041,785 B2
APPLICATION NO. : 15/555429
DATED : August 7, 2018
INVENTOR(S) : Jacobus Lodevicus Martinus Van Mechelen Page 1 of 1

It is certified that error appears in the above-identified patent and that said Letters Patent is hereby corrected as shown below:

On the Title Page

Column 1, (73) Assignee:
"ABB Schweiz AG, Baden (DE)"

Should read:
--ABB Schweiz AG, Baden (CH)--

Signed and Sealed this
Second Day of October, 2018

Andrei Iancu
*Director of the United States Patent and Trademark Office*